(12) United States Patent
Padgurskas et al.

(10) Patent No.: US 10,161,840 B2
(45) Date of Patent: Dec. 25, 2018

(54) DEVICE FOR EVALUATION OF THE WORKING SURFACE FRETTING WEAR CHARACTERISTICS

(71) Applicant: Aleksandras Stulginskis University, Kauno r. (LT)

(72) Inventors: Juozas Padgurskas, Kauno r. (LT); Albinas Andriusis, Kaunas (LT); Ramutis Bansevicius, Kaunas (LT); Algimantas Bubulis, Kaunas (LT); Vytautas Jurenas, Kaunas (LT); Audrius Zunda, Kauno r. (LT)

(73) Assignee: Aleksandras Stulginskis University, Kauno r. (LT)

( * ) Notice: Subject to any disclaimer, the term of this patent is extended or adjusted under 35 U.S.C. 154(b) by 133 days.

(21) Appl. No.: 15/485,230

(22) PCT Filed: Apr. 16, 2015

(86) PCT No.: PCT/LT2015/000005
§ 371 (c)(1),
(2) Date: Apr. 12, 2017

(87) PCT Pub. No.: WO2016/060535
PCT Pub. Date: Apr. 21, 2016

(65) Prior Publication Data
US 2017/0234785 A1 Aug. 17, 2017

(30) Foreign Application Priority Data
Oct. 13, 2014 (LT) .................................... 2014 116

(51) Int. Cl.
*G01N 3/56* (2006.01)

(52) U.S. Cl.
CPC ....... *G01N 3/56* (2013.01); *G01N 2203/0005* (2013.01); *G01N 2203/0051* (2013.01);
(Continued)

(58) Field of Classification Search
CPC ... G01N 3/56; G01N 2203/0051; G01N 19/02
See application file for complete search history.

(56) References Cited

U.S. PATENT DOCUMENTS 3,945,241 A * 3/1976 Brown ..................... G01N 3/56
73/7
4,507,953 A * 4/1985 Vandermeerssche .... G01N 3/56
73/667

(Continued)

*Primary Examiner* — David A Rogers
(74) *Attorney, Agent, or Firm* — Patentagar PLLC; Alexander Rabinovich

(57) ABSTRACT

A device for evaluating working surface fretting wear characteristics comprises a bottom holder with a sample secured thereto, springs displacing in the X and Y direction, multilayer piezo elements moving in the X, Y, and Z directions, a housing, a top plate/holder, a linear air bearing housing, a spherical upper sample, a linear air bearing shaft, a three-way force sensor, a moving support of the flat air bearing and the flat air bearing housing, a high frequency generator, an amplifier, a controller, an electrical filter, a computer, a force sensor signal amplifier, and a flat air bearing. Instead of springs, it can comprise additional multilayer piezo elements moving in the X and Y directions. The device performs testing surface wear under conditions nearer to actual fretting wear conditions, continuously observing friction pair condition changes during testing and evaluating wear characteristics of the tested material more accurately.

12 Claims, 3 Drawing Sheets

(52) U.S. Cl.
CPC ............... *G01N 2203/0623* (2013.01); *G01N 2203/0658* (2013.01)

(56) References Cited

U.S. PATENT DOCUMENTS

| | | | | |
|---|---|---|---|---|
| 5,377,525 | A * | 1/1995 | Hutchinson | G01N 19/02 73/10 |
| 5,969,226 | A * | 10/1999 | Wert | G01N 3/56 73/577 |
| 6,467,330 | B1 * | 10/2002 | Vizintin | G01N 3/56 73/7 |
| 6,601,456 | B1 * | 8/2003 | Davidson | G01N 3/56 73/7 |
| 6,715,336 | B1 * | 4/2004 | Xu | F16C 19/52 73/577 |
| 6,813,960 | B1 * | 11/2004 | Owen | G01N 3/32 73/794 |
| 7,293,448 | B2 * | 11/2007 | Treece | G01N 3/56 451/5 |
| 8,281,666 | B2 * | 10/2012 | Jevons | G01N 3/24 73/818 |
| 8,869,589 | B2 * | 10/2014 | Lappe | G01N 19/02 73/9 |
| 2002/0142920 | A1 * | 10/2002 | Sugimori | C10M 117/04 508/116 |
| 2002/0194895 | A1 * | 12/2002 | Germinario | G01N 19/02 73/9 |
| 2003/0177840 | A1 * | 9/2003 | Corrias | G01N 3/56 73/808 |
| 2007/0017300 | A1 * | 1/2007 | Bushey | G01N 3/02 73/856 |

\* cited by examiner

DEVICE FOR EVALUATION OF THE WORKING SURFACE FRETTING WEAR CHARACTERISTICS

BACKGROUND OF THE INVENTION

1. Field of the Invention

The present device relates to surface wear measurement and is used in the machinery industry. More specifically, the device is intended for an evaluation of working surface fretting wear characteristics.

The surface wear depends on the properties of interacting surfaces and applied loads. Fretting wear is a mechanical wear of surfaces in contact relative to each other in response to small vibratory movements thereof. Those micro movements, depending on the type of interaction, can take place in various directions. An example of that is the mating of a case bearing hole and the outer surface of the bearing cup where radial movements of the bearing cup relative to hole surface are caused by the system eccentricity. The offset value and the character of the movement are subject to the mating pressing force. Because of the axial eccentricity, axial (i.e. along the axis) movements of the bearing cup relative to the hole surface arise. Additionally, the surfaces in contact can move due to bearing ring spinning relative to the hole surface. Under real-life conditions, the micro movements of the surfaces as a result of spinning and axial eccentricity predominantly take place. Also, the surface machine direction and inner structure orientation work upon the intensity of fretting wear. All this means that the ability of a device to examine fretting wear through the micro movements in all the directions and the influence thereof becomes an important advantage of such device.

2. Description of the Related Art

Various methods and devices are known to evaluate wear. A device for testing fretting wear of ball-bearings is disclosed in the U.S. Pat. No. 6,715,336 of Apr. 6, 2004. In the patent, the working surface is treated by pressing a sphere to a plane (Z-direction) by two piezo actuators and moving it horizontally (X-direction). The loads are provided accurately, though only in two directions, therefore it is not possible to evaluate a potential displacement of the surfaces in the third axis (Y) direction.

The Chinese application CN 103 604 713A of Feb. 26, 2014 discloses a friction pair composed of two samples, a flat and a cylindrical (a tube) ones, contacting along a line. The cylindrical sample rests on two other cylindrical samples. The flat sample is attached to a vertical cylindrical rod which is adapted to vibrate in a vertical direction by means of a piezo element. In this way, a multidirectional radial-tangential movement is said to arise. The disclosure shows an uncontrolled and unregulated movement of the contacting surfaces relative each other in two directions (Z and either X or Y).

Known from the Japanese application JP 2005 249462A of Sep. 15, 2005 is a device for a biaxial movement to model fretting wear along X (or Y) and Z axes. In the device, a sphere is pressed to a holder by a piezo actuator and vibrated in the Z-direction, whereas the holder is vibrated in the X-direction on the horizontal plane by another piezo actuator. The device is believed to be the closest analogue (prototype) to the present device. Since there is provided a single piezo element for X and Y, movements along those axes are not independent.

The prototype does not seem to provide the possibility to evaluate the fretting wear through the surface displacement in the third (Y) axis direction, as well as to observe the surface wear continuously during the test. To rectify this disadvantage, a cardinal restructuring the device would be needed, including a reconstruction of a system of fixation of the holder.

Since fretting wear of the surfaces of materials usually takes place in response to simultaneous micro displacement of surfaces in all three directions (X, Y, Z), a need exists for a device capable of the fretting wear characteristics evaluation where three-directional controlled and regulated micro movements of the surfaces relative to each other are provided.

SUMMARY OF THE INVENTION

The object of the invention is to provide means that increases the accuracy of assessment of the surface fretting wear characteristics by expanding the test conditions of the analysed contact and continuously observing the state of the friction pair in the course of the test.

The object of the invention is achieved by providing a device for evaluation of the working surface fretting wear characteristics. The device comprises a housing wherein a fretting wear mechanism is immobilized. The fretting wear mechanism comprises an upper holder wherein a spherical upper workpiece is secured. A sensor interposed between a linear air bearing shaft and the upper holder. A flat bottom workpiece is secured to the bottom holder and a system moving the bottom holder in the X, Y and Z-directions and comprising at least three piezo elements and two springs or five piezo elements is attached thereto. The other end of the piezo element moving in the Z-direction is secured to the moving support of the flat air bearing housing, whereas the other ends of the piezo elements moving in the X and Y-directions are secured to the housing via a flat air bearings, and the springs displacing in the X and Y-directions are secured directly to the housing. Additionally, the piezo elements moving in the X, Y, Z-directions are made multilayer, and the sensor can be acoustic or piezoelectric. Also, a measurement-control unit is comprised of a measurement system and a control system connected to computer, the measurement system comprising interconnected sensor signal amplifier and electric signal filter, whose input is connected to the sensor, and the control system comprising a high frequency generator, a modular controller and amplifier, whose outputs are connected to the piezo elements moving in the X, Y, Z-directions.

DETAILED DESCRIPTION OF THE EMBODIMENT

Figure 1:
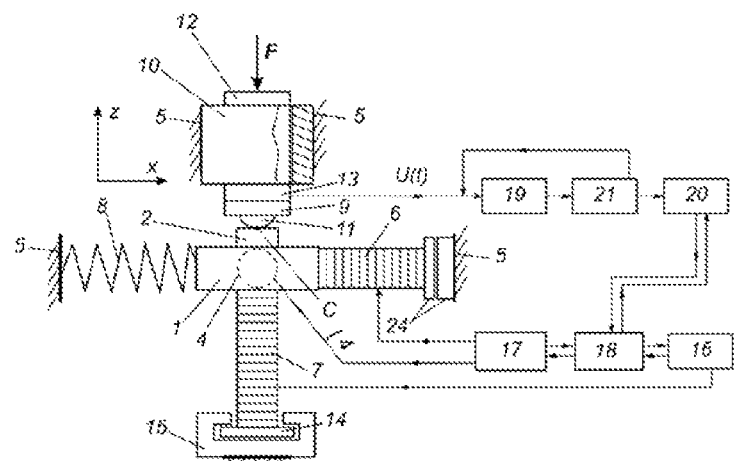
FIG. 1 is a schematic diagram of a side view of the device where the bottom holder moving system comprises three piezo elements and two springs.
Figure 2:
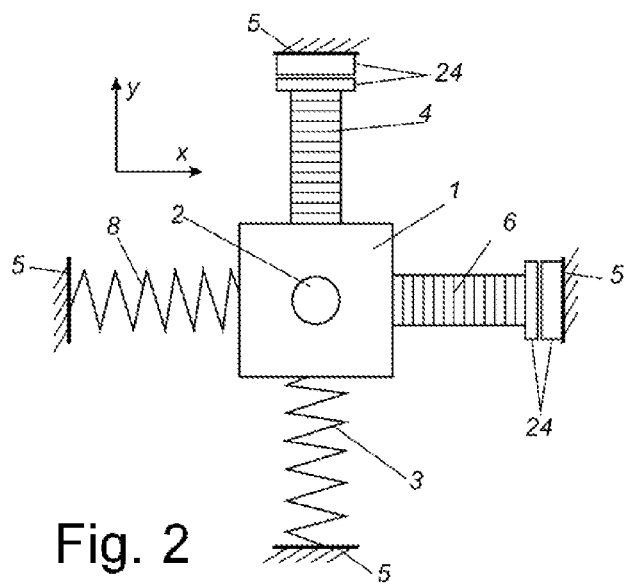
FIG. 2 is a schematic diagram of a top view of the device where the bottom holder moving system comprises three piezo elements and two springs.
Figure 3:
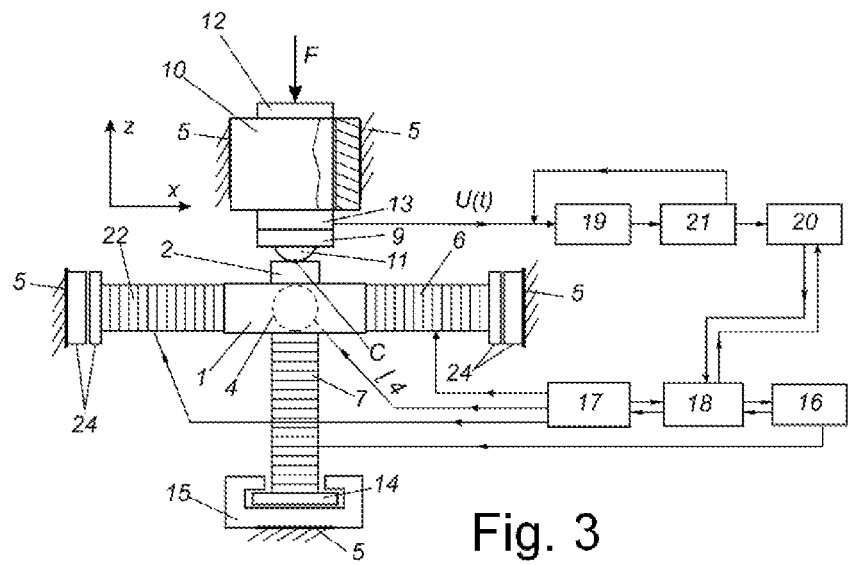
FIG. 3 is a schematic diagram of a side view of the device where the bottom holder moving system comprises five piezo elements.

The device comprises a bottom holder 1 with a flat lower sample (workpiece) 2 secured thereto, a spring 3 displacing in the Y-direction, a multilayer piezo element 4 moving in the Y-direction, a housing 5, a multilayer piezo element 6 moving in the X-direction, a multilayer piezo element 7 moving in the Z-direction, a spring 8 displacing in the X-direction, an upper holder 9, a linear air bearing housing 10, a spherical upper sample (workpiece) 11, a linear air bearing shaft 12, a three-way force sensor 13, a moving support of the flat air bearing 14, a flat air bearing housing 15, a high frequency generator 16, an amplifier 17, a modular controller 18, an electric signal filter 19, a computer 20, a force sensor signal amplifier 21, a multilayer piezo element 22 moving in the X-direction (can be used instead of the spring 8), a multilayer piezo element 23 moving in the Y-direction (can be used instead of the spring 3) and a flat air bearings 24.

Figure 4:
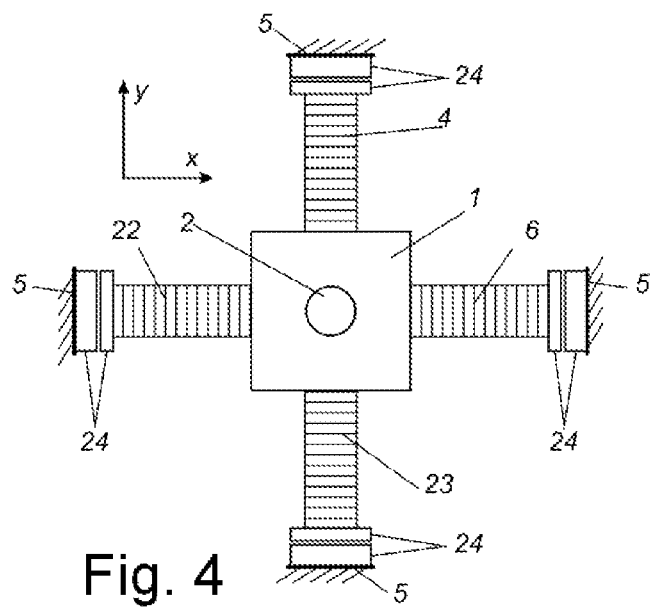
FIG. 4 is a principle schematic diagram of a top view of the device where the bottom holder moving system comprises five piezo elements.
Figure 5:
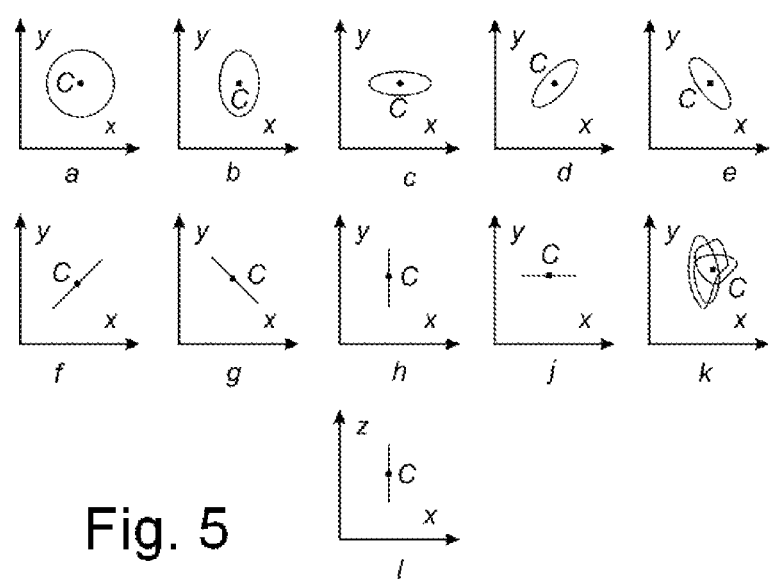
FIG. 5 is a schematic representation of possible movement trajectories of a contact point C of the bottom and upper samples (workpieces).

The device operates as follows:

The spherical upper sample (workpiece) 11 is secured to the upper holder 9, and the bottom sample (workpiece) 2 is secured to the bottom holder 1. When the workload F is applied on the upper workpiece 11 via the linear bearing shaft 12, the upper workpiece presses the bottom workpiece 2 immobilized in the bottom holder 1. Therefore, the load is applied on the friction pair. The load can be static or alternate. The desirable movement schemes are programmed using software program, installed in the computer 20. Multilayer piezoelectric elements 4, 6, 7, 22 and 23 are controlled via the modular controller 18 and the amplifier 17. When the modular controller 18, using high frequency generator 16 and the amplifier 17, actuates the multilayer piezo element 4, it deforms through the inverse piezoelectric effect (it consequently lengthens or shortens), thereby causing the bottom holder 1 and simultaneously the workpiece 2 to move in the Y-direction (see FIG. 5, *h*). The multilayer piezo element 6 is actuated in the same way; it deforms and simultaneously causes the bottom holder 1 and workpiece 2 to move in the X-direction (see FIG. 5, *j*). The modular controller 18 actuates each multilayer piezoelectric element separately. One end of each of the piezo elements 4 and 6 is fastened to the sides of the bottom holder 1 and their other ends are supported in the housing 5 via the flat air bearing 24. The piezo element 7 is actuated by the same principle as the piezo elements 4 and 6, causing the bottom holder 1 and simultaneously the workpiece 2 therewith to move in the Z-direction (see FIG. 5, 1). When the piezo element 7 is actuated, the alternate load acts on the bottom workpiece 2, causing it to move in the Z-direction, and the load at the other end of the multilayer piezo element 7 acts on the flat air bearing housing 15 via the moving support 14 of the flat air bearing. In order to provide 2D or 3D movement to the bottom holder 1 and also to the bottom workpiece 2 (see FIG. 5 *a, b, c, d, e, f, g, k*), the multilayer piezo elements 4, 6, 7 are actuated simultaneously. Springs 3, 8 stabilize the holder 1 in the X-Y plane. Mechanical and tribological processes occurring in the friction pair (contact area C of the bottom and the upper workpiece) are reflected in the three-way sensor 13, the signal thereof (acoustic or piezoelectric) demonstrating the change of the condition in the friction pair in the course of testing. The signal from the sensor 13 is transferred to the sensor signal amplifier 21 through the electrical signal filter 19, and further to the computer 20. If the multilayer piezo elements 22, 23 are used instead of the springs 3, 8 (see FIG. 4), the construction of the fretting abrasion mechanism is more rigid in the X-Y plane, therefore it is possible to perform tests under bigger loads F on the friction pair and create higher amplitude of movement in X and Y directions.

Due to the new totality of the structural elements and the fact that the multilayer piezo element moving in the Z-direction provides the bottom workpiece with the chosen load and the movement which is perpendicular to the holder, and, treated by the bottom holder moving system, the contact point C of the samples performs a complicated 2D or 3D movement within the wide range of amplitudes in the X, Y and Z-directions, the described device, unlike the prior art, is capable of performing testing of the surface wear under conditions that are more proximate to the actual fretting wear conditions, and of continuously observing changes of the condition of the friction pair during the course of testing, relying on indications of the acoustic or piezoelectric sensor 13, and of evaluating simultaneously wear characteristics of the tested material more accurately.

The invention claimed is:

1. A device for the assessment of working surface fretting wear characteristics, said device comprising an upper plate holder mounted in a housing with an upper sample fixed thereto, a bottom plate holder with a flat bottom sample fixed thereto, a computer controlling a measurement and control unit, a measurement system of said unit comprising a three-way force sensor, and a signal amplifier, which has its output connected to said computer, a control system of said unit comprising a signal amplifier connected to a controller connected with a high frequency signal generator and said computer, said signal amplifier controlling a piezoelectric drive, wherein said upper plate holder is attached to said housing via a linear air bearing, said force sensor is installed between said linear air bearing and said upper plate holder, said bottom plate holder has said piezoelectric drive mounted thereto and operating in horizontal X, Y and vertical Z directions, said piezoelectric drive comprising three piezoelectric elements attached to said bottom plate holder directly and attached to said housing via flat air bearings and two springs which are fixed to said housing directly, and said three-way force sensor of said measuring system is connected to said signal amplifier through a signal filter.

2. The device according to claim 1, wherein each of said two piezoelectric elements operates in pair with a spring of said two springs in horizontal X and Y directions, and one piezoelectric element operates in vertical Z direction.

3. The device according to claim 1, wherein said piezoelectric elements of said piezoelectric drive operating in X, Y, Z directions are multilayer.

4. The device according to claim 1, wherein said force sensor is acoustic.

5. The device according to claim 1, wherein controller is made modular and comprises two independently controlled modules, synchronizing work of said piezoelectric elements pairs in X and Y directions.

6. The device according to claim 1, wherein said force sensor is piezoelectric.

7. A device for the assessment of working surface fretting wear characteristics, said device comprising an upper plate holder, mounted in a housing, with an upper sample fixed thereto, a bottom plate holder with a flat bottom sample fixed thereto, a computer controlling a measurement and control unit, a measurement system of said unit comprising a three-way force sensor, and a signal amplifier, which has its output connected to said computer, a control system of said unit comprising a signal amplifier connected to a controller connected with a high frequency signal generator and said computer, said signal amplifier controlling a piezoelectric drive, wherein said upper plate holder is attached to said housing via a linear air bearing, said force sensor is installed between said linear air bearing and said upper plate holder, said bottom plate holder has said piezoelectric drive mounted thereto and operating in horizontal X, Y and vertical Z directions, said piezoelectric drive comprising five piezoelectric elements attached to said bottom plate holder directly and attached to said housing via flat air bearings, and said three-way force sensor of said measuring system is connected to said signal amplifier through a signal filter.

8. The device according to claim 7, wherein four piezoelectric elements work in horizontal X and Y directions in pairs, and one piezoelectric element operates in vertical Z direction.

9. The device according to claim 7, wherein said piezoelectric elements of said piezoelectric drive operating in X, Y, Z directions are multilayer.

10. The device according to claim 7, wherein said force sensor is acoustic.

11. The device according to claim 7, wherein said force sensor is piezoelectric.

12. The device according to claim 7, wherein said controller is made modular and comprises two independently controlled modules, synchronizing work of the piezoelectric elements in X and Y directions.

\* \* \* \* \*